United States Patent [19]

Szonntagh

[11] 4,389,876

[45] Jun. 28, 1983

[54] TEMPERATURE SENSOR AND DETECTOR CELL UTILIZING THE SAME

[75] Inventor: Eugene L. Szonntagh, Flourtown, Pa.

[73] Assignee: Honeywell Inc., Minneapolis, Minn.

[21] Appl. No.: 181,488

[22] Filed: Aug. 26, 1980

[51] Int. Cl.³ .................. G01N 31/00; G01F 1/68; H01C 7/10

[52] U.S. Cl. .................. 73/27 R; 73/204; 73/196; 338/22 R; 204/192 F

[58] Field of Search .......... 73/204, 27 R, 196; 338/22 R, 225 D; 204/192 F

[56] References Cited

U.S. PATENT DOCUMENTS

| | | | |
|---|---|---|---|
| 2,609,470 | 9/1952 | Quinn | 338/22 R |
| 3,186,229 | 6/1965 | Liben | 374/185 X |
| 3,343,004 | 9/1967 | Oushinsky | 338/25 X |
| 3,472,074 | 10/1969 | Glang et al. | 338/25 |
| 3,479,257 | 11/1969 | Shaver | 340/632 X |
| 3,603,134 | 9/1971 | Norem | 73/27 R |
| 3,639,165 | 2/1972 | Rairden | 204/192 F X |
| 3,658,479 | 4/1972 | Heijne et al. | 73/27 R X |
| 3,703,456 | 11/1972 | Cordes | 204/192 F |
| 3,763,026 | 10/1973 | Cordes | 204/192 F |
| 3,900,819 | 8/1975 | Djorup | 73/204 X |
| 3,931,736 | 1/1976 | Olmstead | 73/204 |
| 3,971,247 | 7/1976 | Rodder | 73/204 X |
| 4,011,756 | 3/1977 | Lemos | 73/204 |
| 4,036,053 | 7/1977 | Jenkins | 73/204 |
| 4,068,205 | 1/1978 | Diehl et al. | 338/25 |
| 4,103,275 | 7/1978 | Diehl et al. | 338/25 |
| 4,140,989 | 2/1979 | Baixeras et al. | 338/25 |
| 4,158,166 | 6/1979 | Isenberg | 73/27 R X |
| 4,241,103 | 12/1980 | Ohkubo et al. | 204/192 F |
| 4,283,944 | 8/1981 | Gruner et al. | 73/204 |

FOREIGN PATENT DOCUMENTS

| | | | |
|---|---|---|---|
| 839615 | 6/1960 | United Kingdom | 73/204 |
| 1488012 | 10/1977 | United Kingdom | 73/204 |
| 2025061 | 1/1980 | United Kingdom | 73/204 |
| 2025062 | 1/1980 | United Kingdom | 73/204 |

OTHER PUBLICATIONS

Kingzett's Chemical Encylcopedia by D. Van Nostrand Co., Editor, D. H. Hey, 1966, p. 1017, on Vermiculite.
Condensed Chemical Dictionary, by Arthur and Elizabeth Rose, published by Reinhold Publishing Corp., New York, 1966, pp. 1003, 1004.
Electronics Dictionary; by John Markus, published by McGraw-Hill Book Co., 1978, p. 628.
Webster's Third New International Dictionary, unabridged, by G. & C-Merriam Company, 1961, p. 2544, on Vermiculite.

Primary Examiner—Stephen A. Kreitman
Assistant Examiner—David V. Carlson
Attorney, Agent, or Firm—Lawrence J. Marhoefer; Lockwood D. Burton; Mitchell J. Halista

[57] ABSTRACT

A temperature sensor uses a thin film structure having an RF sputtered layer of a temperature sensitive material forming a thermistor element deposited on an electrically insulating and thermally insulating substrate. The sensor may include a plurality of deposited thermistor layers arranged on both sides of the substrate and having electrical connection means attached thereto. The sensor is arranged on a substrate suitable for inclusion in a detector cell forming a chamber arranged to be connected to a source of fluid flow.

6 Claims, 5 Drawing Figures

U.S. Patent Jun. 28, 1983 4,389,876
PRIOR ART
FIG. 1
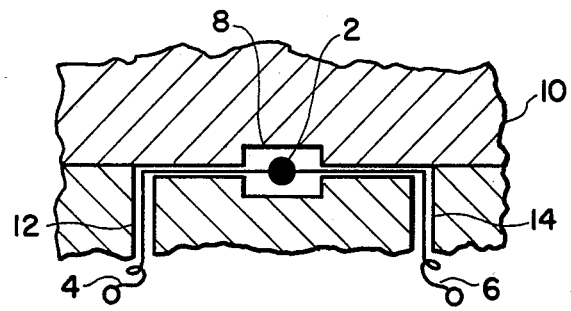
FIG. 2
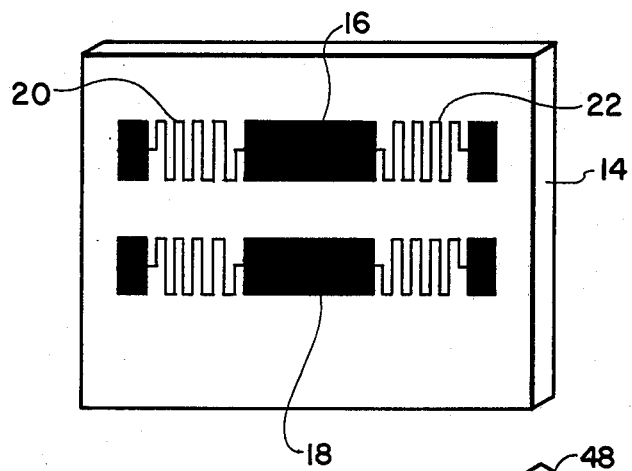
FIG. 3
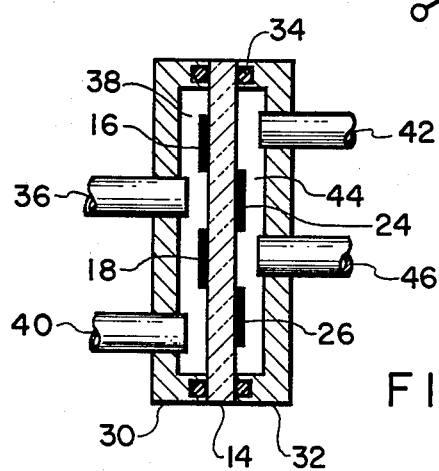
FIG. 5
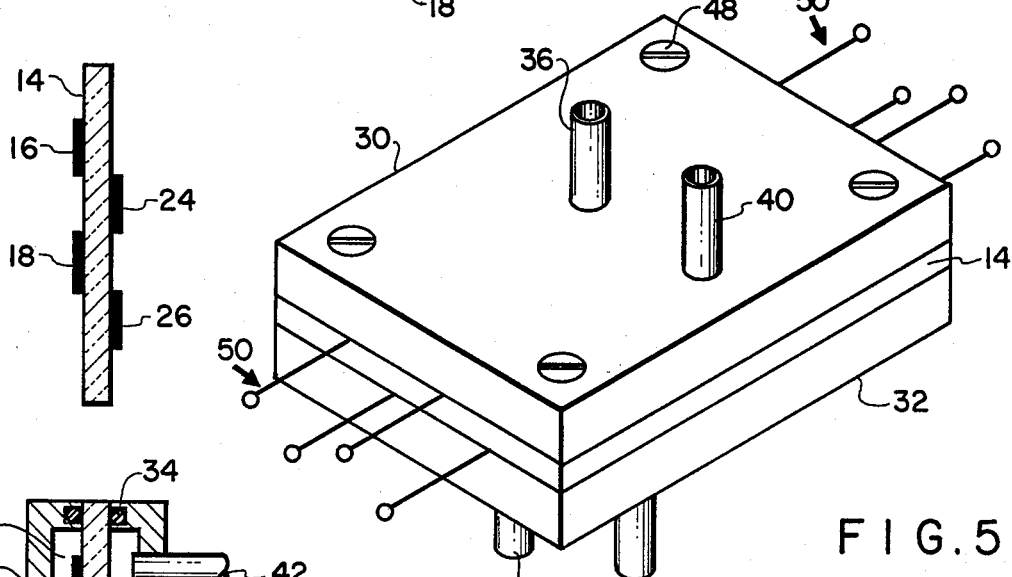
FIG. 4

TEMPERATURE SENSOR AND DETECTOR CELL UTILIZING THE SAME

BACKGROUND OF THE INVENTION

1. Field of the Invention

The present invention relates to temperature sensors. More specifically, the present invention is directed to a temperature sensor utilized as a heat conductivity detector in a detector cell for fluid analysis.

2. Description of the Prior Art

The use of detector cells for determining the conductivity of a fluid passed therethrough is well-known in the art as shown in U.S. Pat. No. 3,243,991. Such cells use an electrically heated element in the form of a thermistor bead arranged within the cell and exposed to the fluid flow whereby the electrical resistance of the thermistor bead changes with the thermal conductivity of the fluid since the heated element loses heat more rapidly to fluids with a high heat conductivity. In most applications the heat conductivity detector cells are provided in pairs with one of the cells being arranged to have the fluid to be analyzed flowing therethrough while the other cell is provided with a comparison or reference fluid flow. The detector cells have been used to measure the concentration of specific components in a fluid and to detect the fluid components successively appearing at the outlet of a separating column of a chromatograph. In such an application, one cell would be provided with the output from a column which output would include the unknown gas and a carrier gas while the other cell would be provided with only a carrier gas flow. Such prior art thermistors and detector cells have several inherent disadvantages. Specifically, the thermistor beads have considerable mass whereby a rapid change in the heat conductivity affect of the different fluids is not reflected by a rapid change in the thermistor characteristics. Since such thermistor beads are often arranged on thin connecting or suspension wires, the structure is sensitive to vibration which causes electrical noise in the output signal. Such a thermistor bead and hanging wire structure is also very fragile, and, the deliberate reproducibility of substantially identical thermistors is virtually impossible. Accordingly, matched pairs of prior art bead thermistors are selected from hundreds of thermistor sensors by expensive electronic matching. The production of such thermistor sensors is also not suited for mass production whereby the cost of the thermistor devices is relatively expensive. Accordingly, it would be desirable to provide a solid state thermistor using solid state technology to enable the mass production of such thermistor devices with extreme uniformity thereof.

SUMMARY OF THE INVENTION

An object of the present invention is to provide an improved temperature sensor in the form of a thin film thermistor element.

Another object of the present invention is to provide an improved detector cell utilizing thin film thermistor temperature sensors.

In accomplishing this and other objects, there has been provided, in accordance with the present invention a temperature sensor thermistor element having a thin film thermistor element deposited on an electrically insulating and thermally insulating substrate. Electrical connections are provided to the thermistor element by electrical leads deposited on the substrate. A detector cell utilizing such a temperature sensor includes a pair of sensor cover elements in contact with the substrate and arranged to peripherally seal the substrate while providing an internal space surrounding the thermistor elements with electrical connections exiting from the detector cell while fluid flow passageways are provided to the internal space.

BRIEF DESCRIPTION OF THE DRAWINGS

A better understanding of the present invention may be had when the following detailed description is read in connection with the accompanying drawings, in which:

FIG. 1 is a cross-sectional illustration of a prior art temperature sensor thermistor and a detector cell utilizing the same, FIG. 2 is a pictorial illustration of a top view of a thermistor structure embodying an example of the present invention, FIG. 3 is an end view of the thermistor structure shown in FIG. 2, FIG. 4 is a cross-sectional illustration of a detector cell utilizing the thermistor structure shown in FIGS. 2 and 3 and FIG. 5 is a pictorial illustration of the external configuration of the detector cell shown in FIG. 4.

DESCRIPTION OF THE PREFERRED EMBODIMENT

In FIG. 1, there is shown a prior art detector cell having a thermistor bead 2 suspended between a pair of thin electrical conductive connecting wires 4 and 6. The thermistor bead is located within a fluid flow cavity 8 formed within a housing 10 providing fluid flow connections (not shown) to the cavity 8 and electrical connecting wire ports 12 and 14 for the connecting wires 4 and 6, respectively. An example of such a thermistor structure is shown in the aforesaid U.S. Pat. No. 3,243,991.

In FIG. 2, there is shown a top view of a thermistor structure embodying an example of the present invention. An electrically insulating and thermally insulating substrate 14 which may be made of any suitable material such as vermiculite, has deposited thereon a pair of ribbon-like layers of suitable thermistor material, e.g., sulfides or oxides of various metals. The substrate 14 is effective to electrically isolate the thermistor elements 16, 18 while preventing heat loss through the substrate. The deposited layers which are shown as layers 16 and 18 are deposited by any suitable material depositing technique, e.g., RF sputtering. While two thermistor elements are shown in the example of FIG. 2, the number of individual thermistors would depend on the particular use and the area of the substrate available for the thermistors. Electrical conductors connected to the ends of the thermistor elements 16, 18 are deposited on the substrate in a square-wave pattern to maximize the length of the electrical conductor whereby to minimize heat losses through the electrical conductor from the thermistor element. Thus, thermistor element 16 has connectors 20 and 22 associated therewith. The ends of the conductors are electrically connected to the thermistor element by welding or soldering in an operation similar to techniques used in making integrated circuits. The material of the leads can be any corrosion resistant electrical conductor with preferably a low thermal coefficient, e.g., Constantan, Kovar, etc.

In FIG. 3, there is shown an end view of the sensor structure shown in FIG. 2. As may be seen from the end view, reference thermistors 24 and 26 may be deposited on the opposite side of the substrate 14 from the measuring thermistors 16 and 18 along with corresponding electrical connections. Further, the reference thermistors 24 and 26 may be staggered with respect to the measuring thermistors 16 and 18 to provide further thermal isolation.

In FIG. 4, there is shown a cross-sectional illustration of a detector cell utilizing the thermistor structure shown in FIGS. 2 and 3. Specifically, the substrate 14 is arranged with the measuring thermistors 16 and 18 on one side thereof and the reference thermistors 24 and 26 on the opposite sides thereof between two havles 30 and 32 of a detector cell housing. The two halves of the detector cell housing 30, 32 are arranged to form respective internal spaces on corresponding sides of the substrate 14. Further, the detector cell halves 30, 32 are provided with sealing rings, e.g., sealing ring 34, located in an edge recess of a force of a corresponding detector cell half, e.g., cell half 32. These sealing members seal against the substrate 14 to provide a fluid-tight seal for the internal spaces of the detector cell.

A first fluid inlet 36 is arranged to be connected between a source of a fluid to be measured and a first internal space or volume 38 formed by the first cell housing half 30 on the measuring side of the substrate 14. A fluid outlet 40 is also connected to the first space 38. Similarly, a reference fluid inlet 42 is connected to the second internal space or volume 44 on the reference side of the substrate 14 within the detector cell housing half 32. Finally, a reference fluid outlet 46 is connected to the internal second space 44 to provide an outlet for the reference fluid.

In FIG. 5, there is shown a pictorial illustration of the exterior configuration of a detector cell shown in FIG. 4. Similar reference numbers have been used in FIG. 5 to denote common elements also shown in FIG. 4. The layered structure of a detector cell is held together with suitable attaching means, such as screws 48. Electrical leads 50 are connected to the respective ends of the deposited electrical conductors of the reference and measuring thermistors and extend out from the detector cell through suitable fluid-tight seals for connection to associated equipment utilizing the thermistor elements. The detector cell of the present invention is used to detect the thermal conductivity of the unknown fluid as well as the reference fluid whereby a change in the rate of heat loss will change the electrical resistance of the thermistor. Such a resistance change can be detected as a representation of a measurement of the constituents of the fluid to be analyzed. The thin film thermistors 16, 18, 24 and 26 are deposited as layers having a thickness of approximately 1000 Angstroms which have very fast response time to thermal conductivity changes in the fluid to be analyzed. Further, the detector cells and the thermistors are produced in a manner which can provide uniform elements for maximum reproducibility. Additionally, the miniaturization of the thermistor element lends itself to the use of extremely small volume cavities for the detector cell to assist in the response time.

Accordingly, it may be seen that there has been provided, in accordance with the present invention, an improved thermistor element and a detector cell utilizing the element.

The embodiments of the invention in which an exclusive property or privilege are claimed is as follows:

1. A temperature detector cell comprising
an electrically insulating and thermally insulating substrate,
a thermistor element means deposited on said substrate,
a first electrical connector means deposited on said substrate and connected to one end of said element means,
a second electrical connector means deposited on said substrate, and connected to the other end of said element means,
cell housing means enclosing said thermistor element means within a volume defined by said housing means,
electrical connection means connected to said first and second electrical connector means and extending out from said housing means and
fluid passage means in said housing means for providing a fluid passage to said volume through said housing means, wherein said substrate is arranged to divide said volume into a first fluid flow path, and a second fluid flow path which is fluid isolated from said first fluid flow path and said thermistor element means includes a first thermistor element deposited on a first side of said substrate and a second thermistor element deposited on a second side of said substrate whereby said first and second thermistor elements are exposed to respective ones of said first and second fluid flow paths and said first electrical connector means including a first electrical connector connected to one end of said first thermistor element and a second electrical connector connected to one end of said second thermistor and said second electrical connector means including a third electrical connector connected to the other end of said first thermistor element and a fourth electrical connector connected to the other end of said second thermistor element and said fluid passage means including a first fluid inlet and a first fluid outlet for admitting a fluid to said first fluid flow path and a second fluid inlet and a second fluid outlet for admitting a fluid to said second fluid flow path.

2. The temperature detector cell as set forth in claim 1 wherein said first and second thermistor elements are each deposited by RF sputtering and have a thickness of approximately 1,000 Angstroms.

3. A temperature detector cell as set forth in claim 1 wherein said substrate is comprised of vermiculite.

4. A temperature detector cell as set forth in claim 1 wherein said first and second thermistor elements are comprised of a deposit of a metal sulfide.

5. A temperature detector cell as set forth in claim 1 wherein said first and second thermistor elements are each comprised of a deposit of a metal oxide.

6. A temperature detector cell as set forth in claim 1 wherein said first and second electrical connector means are each arranged to thermally isolate corresponding ones of said first and second thermistor elements.

* * * * *